(12) United States Patent
Santoro

(10) Patent No.: US 12,384,607 B2
(45) Date of Patent: Aug. 12, 2025

(54) MOUTH GUARD CASE INCLUDING COMPARTMENT FOR STORING AND DISPENSING CLEANING SOLUTION

(71) Applicant: Paper Street Holding, Inc., Chicago, IL (US)

(72) Inventor: Michael Santoro, Chicago, IL (US)

(73) Assignee: Paper Street Holding, Inc., Chicago, IL (US)

( * ) Notice: Subject to any disclaimer, the term of this patent is extended or adjusted under 35 U.S.C. 154(b) by 290 days.

(21) Appl. No.: 17/973,195

(22) Filed: Oct. 25, 2022

(65) Prior Publication Data

US 2024/0182212 A1 Jun. 6, 2024

(51) Int. Cl.
*B65D 47/08* (2006.01)
*A61L 2/18* (2006.01)

(52) U.S. Cl.
CPC ............ *B65D 47/0847* (2013.01); *A61L 2/18* (2013.01)

(58) Field of Classification Search
CPC .............................. B65D 47/0847; A61L 2/18
USPC ....................................................... D3/203.1
See application file for complete search history.

(56) References Cited

U.S. PATENT DOCUMENTS

| | | | | |
|---|---|---|---|---|
| 5,975,362 A | * | 11/1999 | West | B65D 35/285 222/113 |
| D876,820 S | * | 3/2020 | Griffin | D3/203.1 |
| 11,465,821 B1 | * | 10/2022 | Boomsma | B65D 47/06 |
| 2021/0153617 A1 | * | 5/2021 | Doniga | B08B 13/00 |

FOREIGN PATENT DOCUMENTS

JP 2018201713 A * 12/2018

OTHER PUBLICATIONS

JP2018201713A Machine Translation (Year: 2018).*

* cited by examiner

*Primary Examiner* — Spencer E. Bell

(57) ABSTRACT

A mouth guard case including a compartment for storing and dispensing a cleaning solution is disclosed. In one example, an apparatus includes a storage compartment sized and shaped to house a mouth guard and a dispensing compartment reversibly coupled to the storage compartment. The dispensing compartment may include a reservoir to hold a quantity of a cleaning solution and a nozzle to dispense the cleaning solution directly into the storage compartment when the storage compartment is coupled to the dispensing compartment.

20 Claims, 8 Drawing Sheets

MOUTH GUARD CASE INCLUDING COMPARTMENT FOR STORING AND DISPENSING CLEANING SOLUTION

FIELD OF THE INVENTION

The present invention relates generally to sports and dental equipment and relates more specifically to a mouth guard case including a compartment for storing and dispensing cleaning solution.

BACKGROUND OF THE DISCLOSURE

Mouth guards are used in contact sports to prevent trauma to the wearer's teeth and surrounding soft tissue. For instance, mouth guards are commonly used in martial arts, hockey, football, lacrosse, and other sports. However, mouth guards may also be worn for other reasons such as to manage temporomandibular joint (TMJ) disorders or to prevent the wearer from grinding their teeth while sleeping (also known as sleep bruxism). Mouth guards are typically worn over the top teeth and may be fabricated from a variety of materials, with ethylene-vinyl acetate (EVA), silicone, and acrylic being some of the more common materials.

SUMMARY OF THE INVENTION

A mouth guard case including a compartment for storing and dispensing a cleaning solution is disclosed. In one example, an apparatus includes a storage compartment sized and shaped to house a mouth guard and a dispensing compartment reversibly coupled to the storage compartment. The dispensing compartment may include a reservoir to hold a quantity of a cleaning solution and a nozzle to dispense the cleaning solution directly into the storage compartment when the storage compartment is coupled to the dispensing compartment.

In another example, an apparatus includes a storage compartment sized and shaped to house a mouth guard, wherein the storage compartment includes a storage base including an aperture formed in a planar wall of the storage base and a one-way valve positioned in the aperture and a storage lid joined to the planar wall of the storage base by a hinge. The apparatus further includes a dispensing compartment reversibly coupled to the storage compartment, wherein the dispensing compartment includes a reservoir to hold a quantity of a cleaning solution, wherein the reservoir is formed from a first material that is deformable under manual compression, and a nozzle to dispense the cleaning solution directly into the storage compartment through the aperture when the storage compartment is coupled to the dispensing compartment. The apparatus further includes a squeeze guard comprising a frame that is removably fitted around the dispensing compartment, wherein the squeeze guard is formed from a second material that is more rigid than the first material.

BRIEF DESCRIPTION OF THE DRAWINGS

The teachings of the present disclosure can be readily understood by considering the following detailed description in conjunction with the accompanying drawings, in which.

To facilitate understanding, identical reference numerals have been used, where possible, to designate identical elements that are common to the figures.

DETAILED DESCRIPTION

Figure 1:
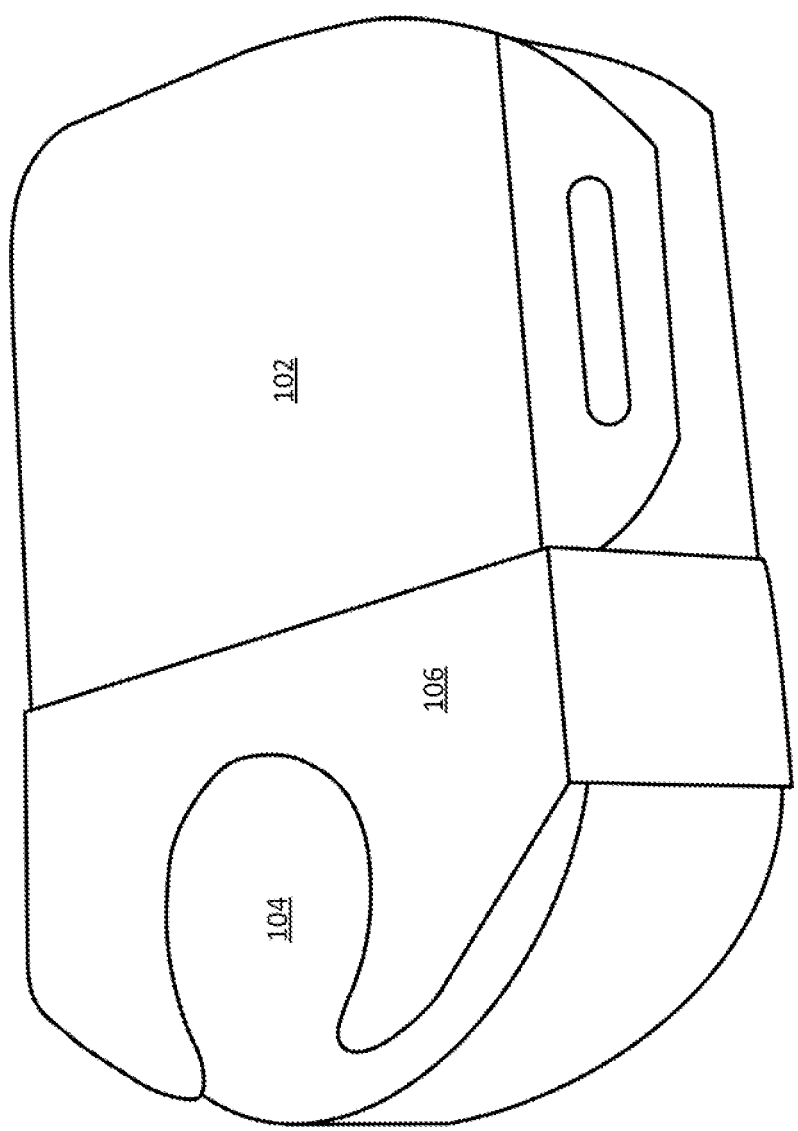
FIG. 1 illustrates an isometric view of one example of a mouth guard case according to the present disclosure.

The present disclosure describes a mouth guard case including a compartment for storing and dispensing cleaning solution. As discussed above, mouth guards are used in contact sports to prevent trauma to the wearer's teeth and surrounding soft tissue. For instance, mouth guards are commonly used in martial arts, hockey, football, lacrosse, and other sports. However, mouth guards may also be worn for other reasons such as to manage temporomandibular joint (TMJ) disorders or to prevent the wearer from grinding their teeth while sleeping (also known as sleep bruxism). Mouth guards are typically worn over the top teeth and may be fabricated from a variety of materials, with ethylene-vinyl acetate (EVA), silicone, and acrylic being some of the more common materials.

Because a mouth guard is worn in the mouth, bacteria and other microorganisms may build up on the surface of the mouth guard if the mouth guard is not properly and regularly cleaned. This may be especially true if the mouth guard is placed in a protective case without being cleaned; the bacteria and microorganisms may multiple more quickly in the dark, enclosed space of the mouth guard case. These bacteria and microorganisms may make the wearer sick.

Examples of the present disclosure provide a mouth guard case that includes a compartment for storing and dispensing a cleaning solution. In one example, the mouth card case comprises three main components that may be assembled to provide a protective enclosure in which a mouth guard may be simultaneously stored and cleaned. The three main components may include a storage compartment for storing a mouth guard, a dispensing compartment for storing and dispensing a cleaning solution, and a squeeze guard.

The storage compartment may be sized and shaped to house a mouth guard. The dispensing compartment may be sized and shaped to hold a quantity of cleaning solution for cleaning the mouth guard. The dispensing compartment may be removably coupled to the storage compartment in order to dispense the cleaning solution directly into the storage compartment. For instance, when compression is applied to the dispensing compartment (e.g., by manually squeezing) while the dispensing compartment is coupled to the storage compartment, the cleaning solution may be expelled from the dispensing compartment and into the storage compartment. When empty, the dispensing compartment may be removed or disconnected from the storage compartment to be refilled with new cleaning solution. The squeeze guard may comprise a rigid frame that fits around at least a portion of the dispensing compartment in order to prevent the dispensing compartment from being compressed accidentally (e.g., during transport, storage, or handling). The squeeze guard may be removed when the mouth guard is to be cleaned.

Although the following discussion makes reference to the storage and cleaning of mouth guards such as those used for contact sports, it will be appreciated that the example cases described herein could also be used to store and clean other types of devices that are removably worn in a user's mouth, such as dental retainers, tray aligners, and dentures. The mouth guard case disclosed herein allows a cleaning solution to be easily stored together with the mouth guard case, such that when a mouth guard is placed inside the mouth guard case, the cleaning solution can be dispensed directly into the storage area, allowing the mouth guard to be cleaned and protected against the growth of bacteria and microorganisms that may make the wearer sick. These and other aspects of the present disclosure are discussed in greater detail below in connection with the examples of FIGS. 1-8.

FIG. 1 illustrates an isometric view of one example of a mouth guard case 100 according to the present disclosure. The example shown in FIG. 1 illustrates the mouth guard case 100 fully assembled, i.e., with the storage compartment 102 and the dispensing compartment 104 connected to each other and the squeeze guard fitted 106 around the outside of the dispensing compartment 104. The mouth guard case 100 may be assembled in the manner shown in FIG. 1 when the mouth guard case 100 is being transported, handled, or is simply storing a mouth guard without cleaning the mouth guard. Alternatively, the mouth card case 100 could also be assembled in the manner shown in FIG. 1 after the cleaning solution has been dispensed into the storage compartment 102 and is actively cleaning a mouth guard inside the storage compartment 102.

Figure 2:
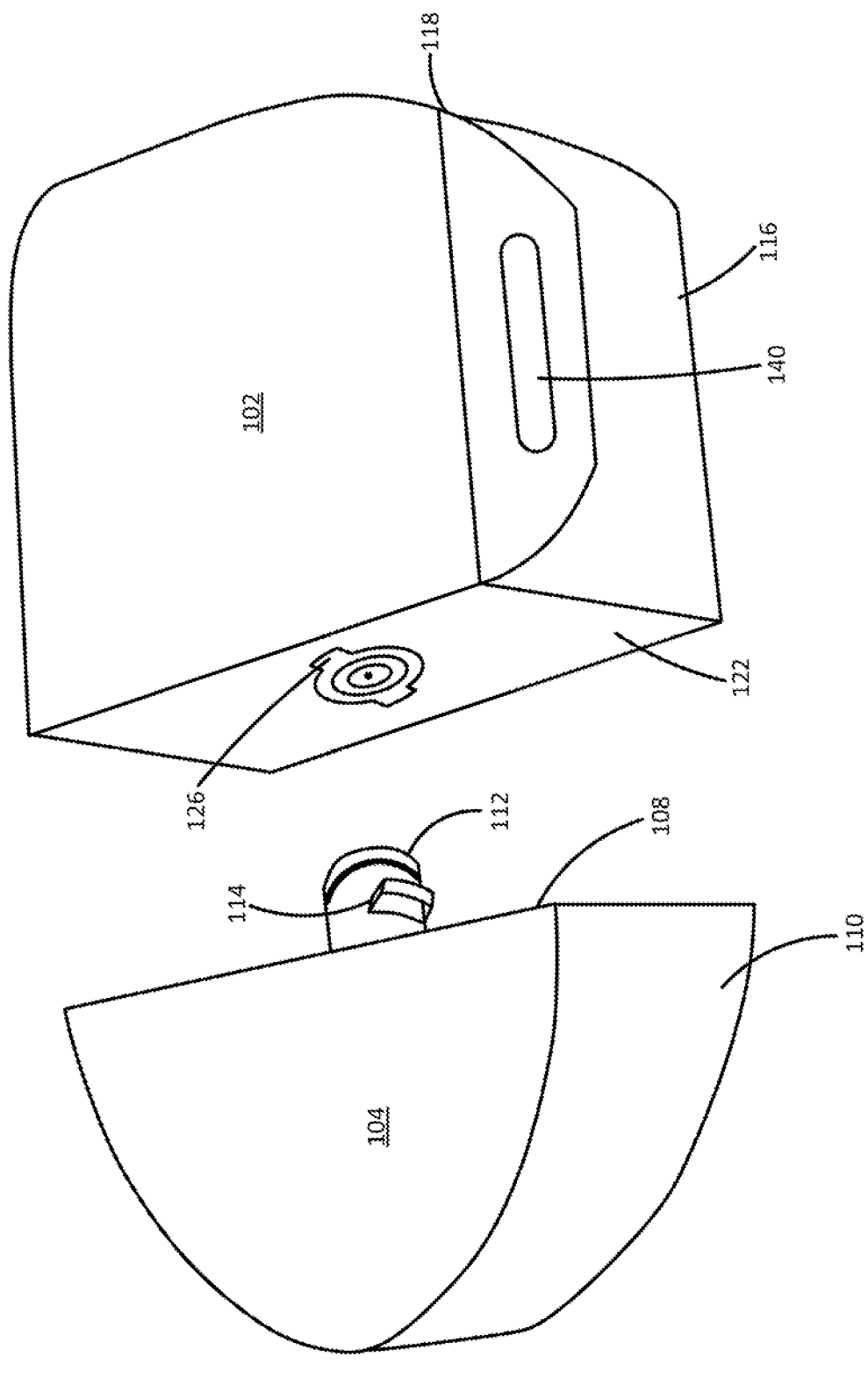
FIG. 2 illustrates an exploded view of some of the components of the mouth guard case illustrated in FIG. 1.
Figure 3:
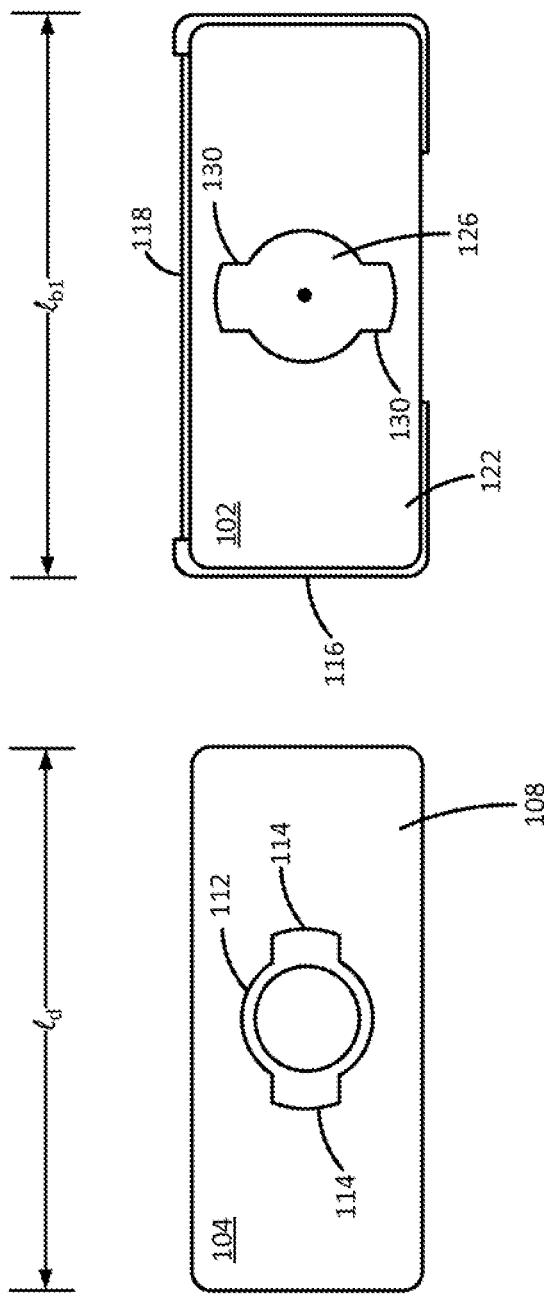
FIG. 3 illustrates side plan views of surfaces of the storage compartment and dispensing compartment of FIGS. 1 and 2.

FIG. 2 illustrates an exploded view of some of the components of the mouth guard case 100 illustrated in FIG. 1. More specifically, FIG. 2 illustrates the storage compartment 102 and the dispensing compartment 104 and the mechanisms that help to removably couple the storage compartment 102 to the dispensing compartment 104. FIG. 3 illustrates side plan views of facing surfaces of the storage compartment 102 and dispensing compartment 104 of FIGS. 1 and 2.

Referring simultaneously to FIGS. 2 and 3, the dispensing compartment 104 may generally comprise a reservoir 110 and a nozzle 112. The reservoir 110 has a hollow interior volume that can store a quantity of cleaning solution for cleaning a mouth guard. In one example, the cleaning solution comprises a liquid cleaning solution, such as mouthwash, a solution of hydrogen peroxide and/or vinegar, a human-safe over the counter chemical cleaner (e.g., such as sodium hypochlorite in a liquid or tablet form that is dissolved in water), or the like. The reservoir 110 may be formed from a semi-flexible, BPA-free plastic or rubber. For instance, the plastic may be deformable under manual compression, such as by a user squeezing the reservoir 110.

In one example, the reservoir 110 includes at least one flat, planar wall 108. Positioned approximately midway along the length $\ell_d$ of the planar wall 108 is the nozzle 112. The nozzle 112 facilitates dispensing of the cleaning solution from the reservoir 110 when the reservoir 110 is under compression. In one example, the nozzle 112 has a cylindrical shape having a substantially circular cross section. However, as shown more clearly in FIG. 3, the nozzle 110 may include at least one tab 114 protruding radially outward from the circumference of the circular cross section. The tab(s) 114 may help to couple the dispensing compartment 104 to the storage compartment 102 in a manner that prevents accidental separation, as discussed in further detail below.

Figure 4:
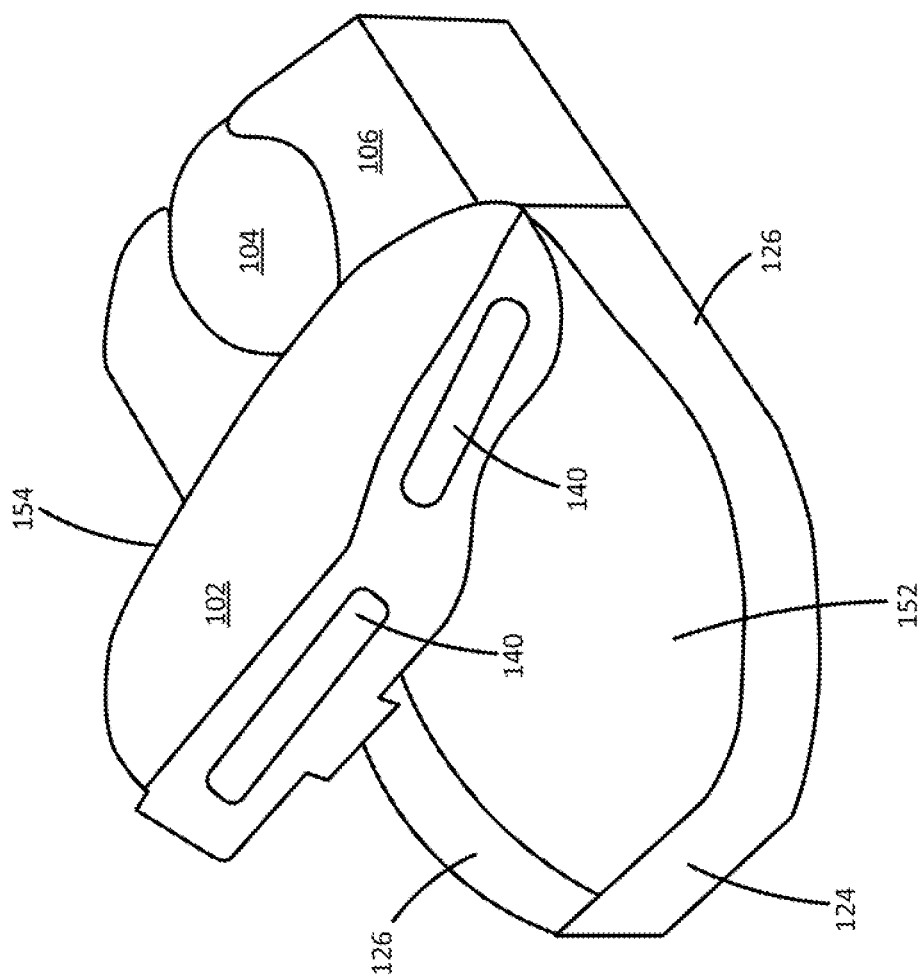
FIG. 4 illustrates an isometric view of the fully assembled mouth guard case of FIG. 1 showing the storage compartment in an open position (e.g., as opposed to the closed position illustrated in FIG. 1)
Figure 5:
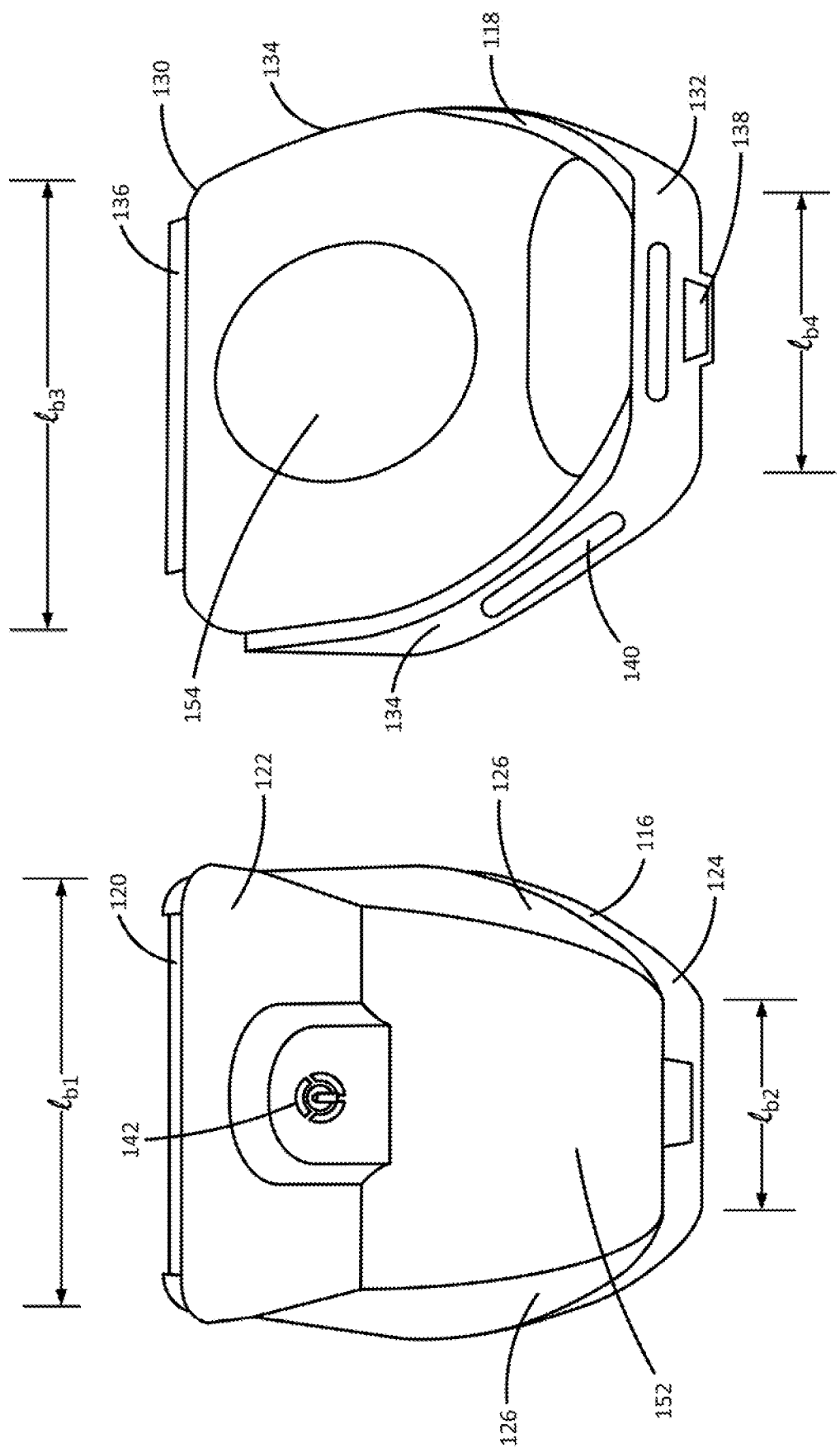
FIG. 5 illustrates top plan views of the storage base and the storage lid of the storage compartment of FIG. 4 in more detail.

The storage compartment 102 may comprise a container that is sized and shaped to hold a mouth guard. In one example, the container comprises a hollow interior volume that is defined between a storage base 116 and a storage lid 118. Further details of the storage base 116 and the storage lid are illustrated in FIGS. 4 and 5. FIG. 4 illustrates an isometric view of the fully assembled mouth guard case 100 of FIG. 1 showing the storage compartment 102 in an open position (e.g., as opposed to the closed position illustrated in FIG. 1). FIG. 5 illustrates top plan views of the storage base 116 and the storage lid 118 of the storage compartment 102 of FIG. 4 in more detail.

As shown in FIG. 5, the storage base 116 is generally sized and shaped to hold a mouth guard. For instance, the storage base 116 may include at least a first flat, planar wall 122. The storage base 116 may also include a second flat, planar wall 124. The length $\ell_{b1}$ of the first planar wall 122 may be longer than a length $\ell_{b2}$ of the second planar wall 124. Side walls 126 connecting the first planar wall 122 to the second planar wall 124 may therefore define a tapered shape that is widest at the first planar wall 122 and narrowest at the second planar wall 124.

As shown in FIG. 5, an edge of the first planar wall 122 (i.e., the edge that is not connected to a side wall 126 or to the bottom 152 of the storage base 116) may include a groove 120 formed along at least a portion of the length $\ell_{b1}$.

The first planar wall 122 may further include an aperture 126. As illustrated in FIG. 3 (which illustrates the outside surface of the first planar wall 122, or the surface of the first planar wall 122 that faces the dispensing compartment 104), the opening of the aperture 126 may have a generally circular shape. However, the generally circular shape may include at least one notch 130 protruding radially outward from the circular shape and being sized and shaped to accommodate the tab(s) 114. The notch(es) 130 helps to lock the dispensing compartment 104 to the storage compartment 102 when the dispensing compartment 104 and the storage compartment 102 are coupled, as discussed in further detail below. A one-way valve 142 (e.g., a rubber gasket), illustrated in FIG. 5, may be positioned within the aperture 126.

As also illustrated in FIG. 5, the storage lid 118 has a similar size and shape to the storage base 116; however, the perimeter of the storage lid 118 may be slightly larger than the perimeter of the storage base 116 (i.e., so that the storage lid 118 can fit and seal over the top of the storage base 116 when the storage compartment 102 is in a fully closed position). In one example, the storage lid 118 comprises a hinged edge 130, a substantially flat, planar wall 132, side walls 134, and a top 154. The length $\ell_{b3}$ of the hinged edge 130 may be longer than a length $\ell_{b4}$ of the planar wall 132. The side walls 134 connecting the hinged edge 130 to the planar wall 132 may therefore define a tapered shape that is widest at the hinged edge 130 and narrowest at the planar wall 132.

The hinged edge 130 may include a tongue 136. The tongue 136 may extend along most of the length $\ell_{b3}$ of the hinged edge 130. A lip 138 may be formed at approximately the midpoint of the length $\ell_{b4}$ of the planar wall 132. Additionally, as shown in greater detail in FIG. 4, the planar wall 132 and each side wall 134 also include an aperture 140 formed therein. In one example, each of the planar wall 132 and the each side wall 134 includes a single aperture 140; however, in other examples, more or fewer apertures 140 may be included without departing from the scope of the present disclosure. Furthermore, in some examples, the planar wall 132 may include a greater number of apertures 140 than either of the side walls 134, or the side walls 134 may include greater numbers of apertures than the planar wall 132. In other examples, the planar wall 132 may include no apertures 140, or the side walls 132 may include no apertures 140. In one example, the apertures 140 may have an elongate, elliptical shape. However, in other examples, the apertures 140 may have different shapes.

The storage lid 118 may be attached to the storage base 116 by fitting the tongue 136 on the storage lid 118 into the groove 120 on the storage base 116, thereby creating a hinge. The hinge may allow the storage compartment 102 to be opened (as shown in FIG. 4) and closed (as shown in FIG. 1). Although the figures illustrate a hinge formed by a tongue and groove, other types of hinged mechanisms are also possible.

In one example, the lip 138 on the storage lid 118 may catch on a portion of the second planar surface 124 of the storage base 116 when the storage compartment 102 is in a fully closed position, in order to securely seal the storage compartment 102. In the fully closed position, the apertures 140 in the storage lid 118 may cover the second planar surface 124 and side walls 126 of the storage base 116, i.e., such that nothing can pass through the apertures 140 and into or out of the storage compartment 102. However, the lip 138 may also allow the storage lid 118 to be propped up above the second planar surface 124 of the storage base, which may allow air to pass through the apertures 140 and into or out of the storage compartment 102. This may be useful for venting a mouth guard (or other apparatus) housed within the storage compartment 102.

The dispensing compartment 104 may be coupled to the storage compartment 102 by inserting the nozzle 112 of the dispensing compartment 104 through the aperture 126 in the storage base 116 of the storage compartment 102. For instance, the nozzle 112 may be inserted through the aperture 126 by aligning the tab(s) 114 on the nozzle 112 with the notch(es) 130 of the aperture 126. The dispensing compartment 104 may then be turned either clockwise or counterclockwise, so that the tab(s) 114 are no longer aligned with the notch(es) 130, thus reversibly locking the dispensing compartment 104 in place. It will be appreciated, however, that other mechanisms for coupling the dispensing compartment 104 to the storage compartment 102 may be used. For instance, the nozzle 112 may include threads (e.g., similar to a screw), and the aperture 126 may include a threaded passage to engage the threads on the nozzle 112. In another example, a friction fit may allow the nozzle 112 and aperture 126 to be reversibly engaged. An O-ring or similar type gasket may be installed on the nozzle 112 to ensure a leak-proof connection to the storage compartment 102.

As discussed above, when a mouth guard housed within the storage compartment 102 is to be cleaned, cleaning solution contained within the dispensing compartment 104 may be dispensed by manually compressing (e.g., squeezing) the dispensing compartment 104, which forces the cleaning solution through the nozzle 112 and into the storage compartment 102.

In order to prevent the cleaning solution from being dispensed accidentally (e.g., while the mouth guard case 100 is being transported, or the storage compartment 102 is vented as described above), the squeeze guard 108 may be fitted over the dispensing compartment 104. In one example, the squeeze guard 108 may comprise a frame that is formed from a material that is more rigid than the material from which the dispensing compartment 104 is formed (e.g., is not easily deformable under manual compression).

Figure 6:
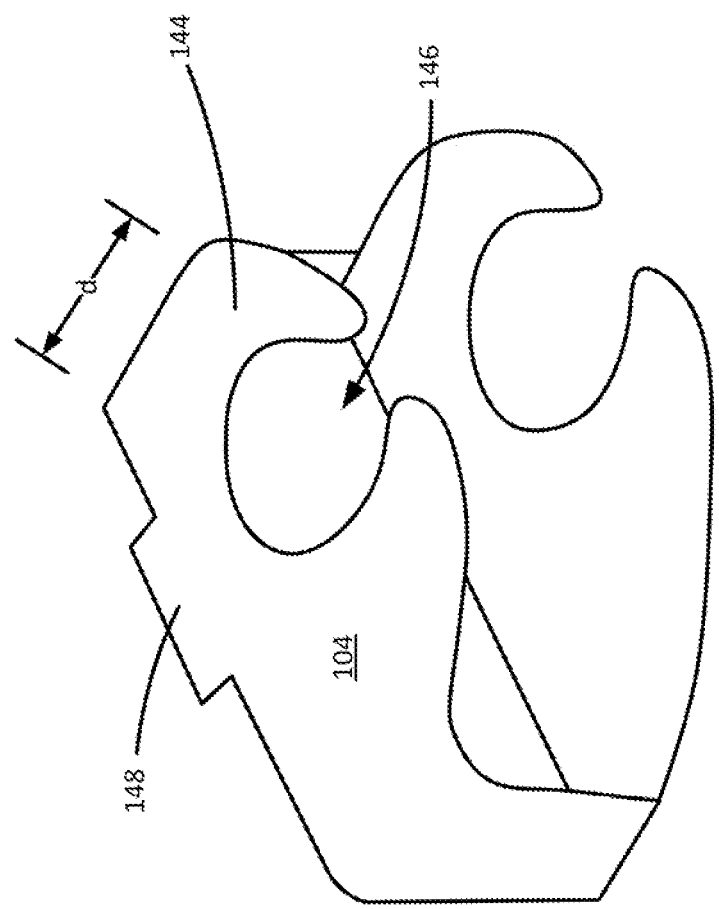
FIG. 6 illustrates an isometric view of one example of the squeeze guard of FIG. 1.

FIG. 6, for instance, illustrates an isometric view of one example of the squeeze guard 108 of FIG. 1. As illustrated, the squeeze guard 108 may comprise a frame 144 having a substantially rectangular opening 146. The inner dimensions of the opening may be slightly larger than the outer dimensions of the dispensing compartment 104, such that the squeeze guard 108 can be fitted around the outside of the dispensing compartment (as shown in FIG. 1). A depth d of the rectangular opening 146 may be sized such that most of the dispensing compartment 104 will fit within the frame 144; however, in some examples, the frame 144 does not fit around the storage compartment 102. However, in one example, the squeeze guard may include a tab 148 which engages a notch in an underside of the storage compartment's storage base 116.

Figure 7:
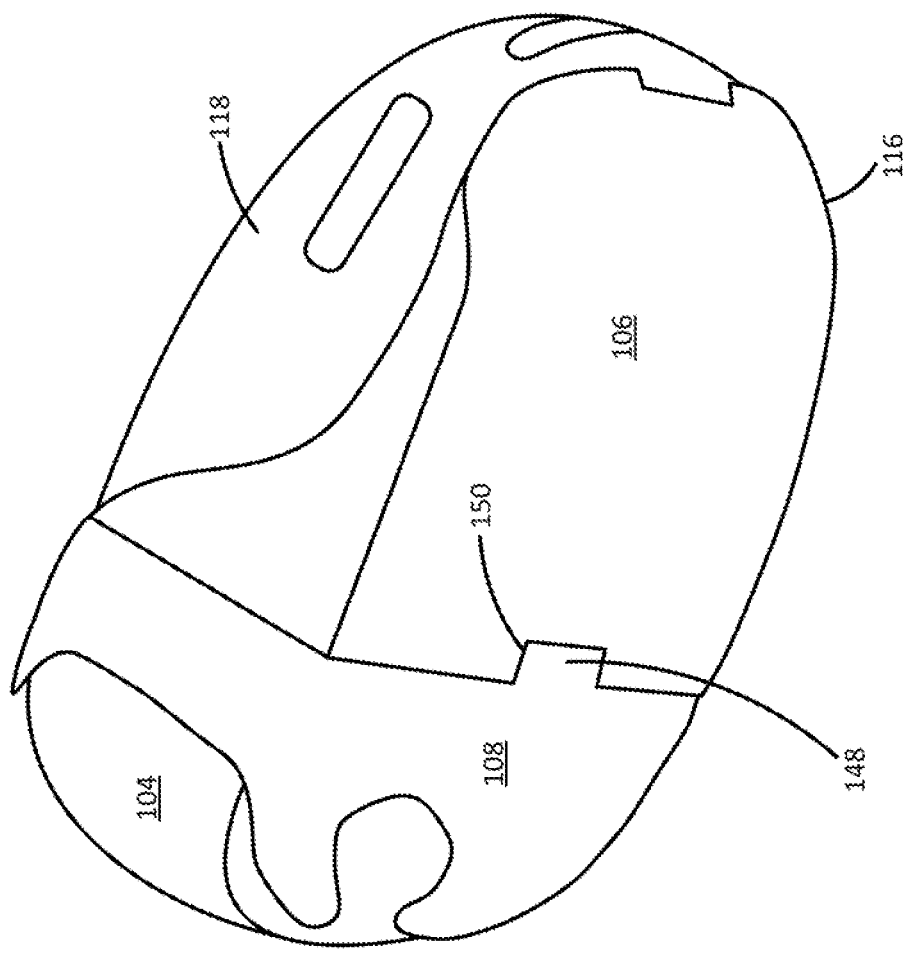
FIG. 7 illustrates an isometric view of the mouth guard case showing the tab of FIG. 6 engaged with a notch in the underside of the storage base of the storage compartment.

FIG. 7, for instance, illustrates an isometric view of the mouth guard case 100 showing the tab 148 of FIG. 6 engaged with a notch 150 in the underside of the storage base 116 of the storage compartment 102. When the tab 148 engages the notch 150, the squeeze guard 108 may be held in place (e.g., so that the squeeze guard 108 does not accidentally slip off the mouth guard case 100).

In one example, the squeeze guard may be formed of a rigid plastic or other material that is more rigid than the material from which the dispensing compartment is formed (e.g., is not easily deformable under manual compression).

Figure 8:
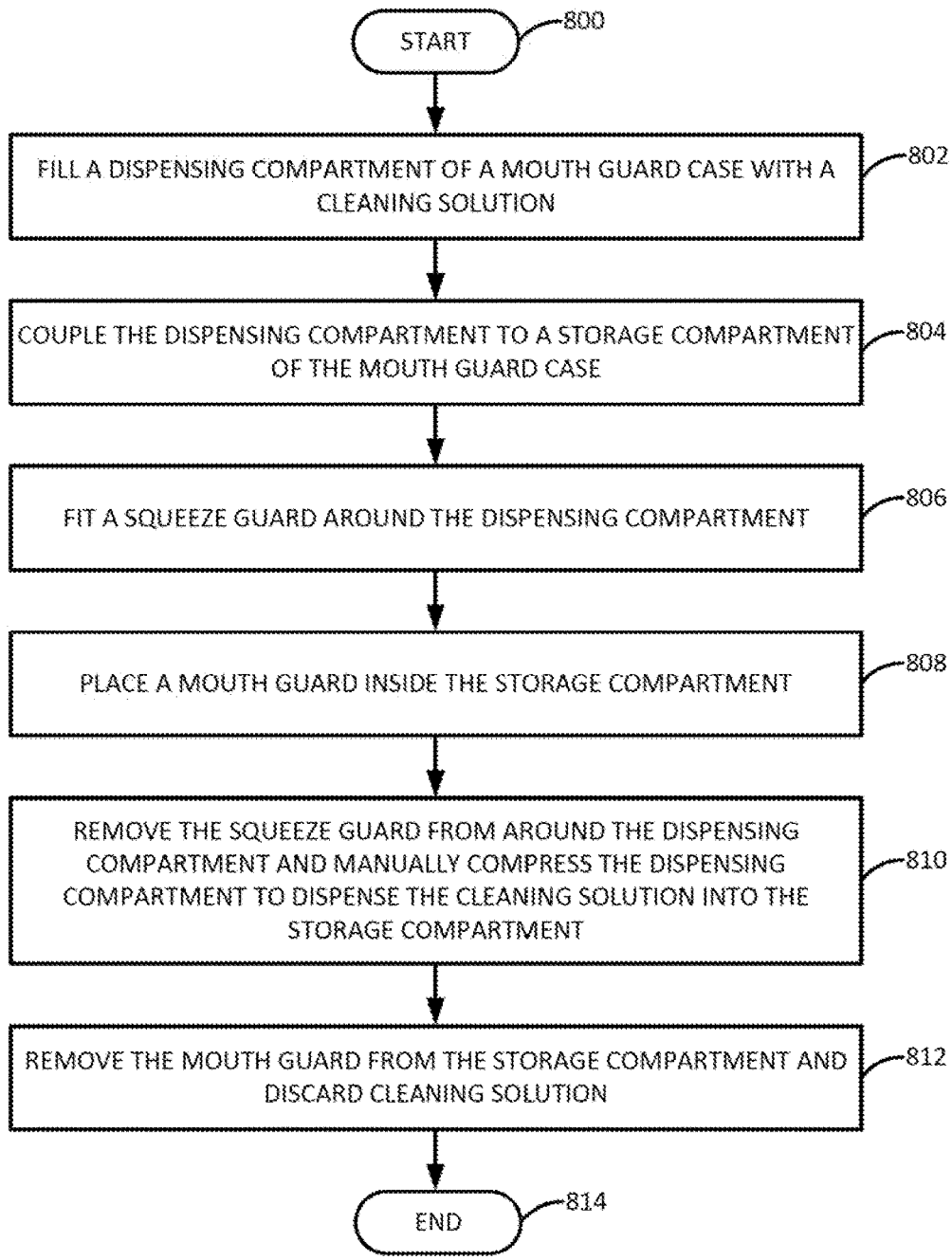
FIG. 8 is a flow diagram illustrating one example of a method for cleaning a mouth guard, according to embodiments of the present disclosure.

FIG. 8 is a flow diagram illustrating one example of a method 800 for cleaning a mouth guard, according to embodiments of the present disclosure. The method 800 begins in step 802 and proceeds to step 804.

In step 804, a dispensing compartment of a mouth guard case, such as the dispensing compartment 104 of the mouth guard case 100 described above, may be filled with a cleaning solution. The cleaning solution may comprise, for example, a liquid cleaning solution such as mouthwash, a solution of hydrogen peroxide and/or vinegar, a human-safe over the counter chemical cleaner (e.g., such as sodium hypochlorite in a liquid or tablet form that is dissolved in water), or the like.

In step 806, the dispensing compartment of the mouth guard case may be coupled to a storage compartment of the mouth guard case, such as the storage compartment 102 of the mouth guard case 100 described above. In one example, the dispensing compartment and the storage compartment may comprise two separate and separable pieces that can be reversibly coupled. A one-way valve in an aperture of the storage compartment may prevent the cleaning solution from flowing into the storage compartment.

In step 808, a squeeze guard, such as the squeeze guard 108 of the mouth guard case 100 described above, may be fitted around the dispensing compartment. The squeeze guard may be held in place by a tab on a frame of the squeeze guard that engages a notch in an underside of the storage compartment. The squeeze guard may be formed from a rigid material that does not deform easily under manual compression. Thus, the squeeze guard may prevent accidental compression of the dispensing compartment and dispensing of the cleaning solution into the storage compartment.

In step 810, a mouth guard may be placed inside the storage compartment of a mouth guard case. The storage compartment may be fully closed after the mouth guard is placed inside, e.g., such that there is no venting of air into or out of the storage compartment.

In step 812, the squeeze guard may be removed from around the dispensing compartment, and the dispensing compartment may be compressed manually (e.g., squeezed) to dispense the cleaning solution into the storage compartment. Dispensing of the cleaning solution into the storage compartment while a mouth guard is housed within the storage compartment will allow the mouth guard to be soaked in the cleaning solution, thereby removing bacteria and microorganisms that may be present on the surface of the mouth guard. The amount of time for which the mouth guard is soaked in the cleaning solution may vary depending upon the ingredients of the cleaning solution. For instance, a container in which the cleaning solution was contained before the dispensing compartment was filled may provide a recommended time period for soaking the mouth guard in the cleaning solution.

In step 814, the mouth guard may be removed from the storage compartment, and the cleaning solution that was dispensed into the storage compartment may be discarded.

The method 800 may end in step 816.

The various components of the mouth guard case (i.e., storage compartment, dispensing compartment, and squeeze guard) may be washed prior to subsequent use. Additionally, the storage compartment may be used (with or without the dispensing compartment and squeeze guard attached) to transport and/or store the clean mouth guard.

Although various embodiments which incorporate the teachings of the present disclosure have been shown and described in detail herein, those skilled in the art can readily devise many other varied embodiments that still incorporate these teachings. In addition, while various embodiments have been described above, it should be understood that they have been presented by way of example only, and not limitation. Thus, the breadth and scope of a claimed embodiment should not be limited by any of the above-described exemplary embodiments, but should be defined only in accordance with the following claims and their equivalents.

What is claimed is:

1. An apparatus, comprising:
   a storage compartment sized and shaped to house a mouth guard, wherein the storage compartment comprises:
      a storage base including a circular opening and a notch protruding radially outward from the circular opening;
      a storage lid joined by a hinge to the storage base, wherein a perimeter of the storage lid is larger than a perimeter of the storage base, and wherein the storage lid comprises:
         a top;
         a hinged edge coupled to the top and having a first length;
         a planar wall coupled to the top, opposite the hinged edge, and having a second length; and
         two side walls connecting the hinged edge to the planar wall such that the top, the hinged edge, the planar wall, and the two side walls collectively define a tapered shape that is widest at the hinged edge and narrowest at the planar wall;
         a plurality of apertures formed in the two side walls; and
         a lip formed in the planar wall, wherein the lip is sized and shaped to selectively engage the storage base in either of a first position that prevents air from passing through the plurality of apertures and a second position that allows air to pass through the plurality of apertures; and
   a dispensing compartment reversibly coupled to the storage compartment, wherein the dispensing compartment comprises:
      a reservoir to hold a quantity of a cleaning solution; and
      a nozzle to dispense the cleaning solution directly into the storage compartment when the storage compartment is coupled to the dispensing compartment,
      wherein the nozzle further comprises:
         a cylindrical shape having a circular cross section; and
         a tab protruding radially outward from the circular cross section,
      wherein an alignment of the tab with the notch allows the nozzle to be inserted into the circular opening, and a rotation of the dispensing compartment that moves the tab away from the notch locks the dispensing compartment to the storage compartment.

2. The apparatus of claim 1, wherein the storage base comprises:
   a bottom;
   a first planar wall coupled to the bottom and having a first length;
   a second planar wall coupled to the bottom and having a second length that is shorter than the first length of the first planar wall; and
   two side walls coupled to the bottom and connecting the first planar wall to the second planar wall, such that the first planar wall, the second planar wall, and the two side walls of the storage base collectively define a tapered shape that is widest at the first planar wall and narrowest at the second planar wall.

3. The apparatus of claim 2, wherein the circular opening is formed in an outward facing side of the first planar wall.

4. The apparatus of claim 3, further comprising:
   a one-way valve positioned in the circular opening.

5. The apparatus of claim 2, wherein an edge of the first planar wall that is opposite the bottom forms part of the hinge.

6. The apparatus of claim 1, wherein the hinged edge forms part of the hinge.

7. The apparatus of claim 1, wherein the planar wall includes the lip that is sized and shaped to engage the storage base to hold the storage compartment in a closed position.

8. The apparatus of claim 1, further comprising:
   a squeeze guard comprising a frame that is removably fitted around the dispensing compartment.

9. The apparatus of claim 8, wherein the squeeze guard includes a tab sized and shaped to engage a notch in an underside of the storage compartment, wherein the notch in the underside of the storage compartment is separate from the notch protruding radially outward from the circular opening in the storage compartment.

10. The apparatus of claim 1, wherein the reservoir is formed from a material that is deformable under manual compression.

11. The apparatus of claim 10, wherein the material is one of: rubber or a plastic that is free of Bisphenol A.

12. An apparatus, comprising:
   a storage compartment sized and shaped to house a mouth guard, wherein the storage compartment comprises:
      a storage base including an aperture formed in a planar wall of the storage base and a one-way valve positioned in the aperture; and
      a storage lid joined to the planar wall of the storage base by a hinge and including a plurality of apertures and a lip, wherein the lip is sized and shaped to selectively engage the storage base in either of a first position that prevents air from passing through the plurality of apertures and a second position that allows air to pass through the plurality of apertures;

a dispensing compartment reversibly coupled to the storage compartment, wherein the dispensing compartment comprises:
- a reservoir to hold a quantity of a cleaning solution, wherein the reservoir is formed from a first material that is deformable under manual compression; and
- a nozzle to dispense the cleaning solution directly into the storage compartment through the aperture formed in the planar wall of the storage base when the storage compartment is coupled to the dispensing compartment; and a squeeze guard comprising a frame that is removably fitted around the dispensing compartment, wherein the squeeze guard is formed from a second material that is more rigid than the first material.

13. The apparatus of claim 12, wherein the squeeze guard includes a tab sized and shaped to engage a notch in an underside of the storage compartment.

14. The apparatus of claim 12, wherein the storage compartment is formed from a plastic.

15. The apparatus of claim 12, wherein the aperture formed in the planar wall of the storage base is sized and shaped to receive the nozzle of the dispensing compartment.

16. The apparatus of claim 15, wherein the nozzle comprises:
- a cylindrical shape having a circular cross section; and
- a tab protruding radially outward from the circular cross section.

17. The apparatus of claim 16, wherein the aperture formed in the planar wall of the storage base comprises:
- a circular opening; and
- a notch protruding radially outward from the circular opening, wherein the notch is sized and shaped to accommodate the tab, wherein an alignment of the tab with the notch allows the nozzle to be inserted into the aperture formed in the planar wall of the storage base, and a rotation of the dispensing compartment that moves the tab away from the notch locks the dispensing compartment.

18. The apparatus of claim 12, wherein the first material is one of: rubber or a plastic that is free of Bisphenol A.

19. The apparatus of claim 12, wherein the second material is a plastic.

20. The apparatus of claim 12, wherein the reservoir is refillable.

* * * * *